(12) United States Patent
Newton et al.

(10) Patent No.: US 11,291,773 B2
(45) Date of Patent: *Apr. 5, 2022

(54) MULTIPLE DOSAGE INJECTOR WITH ROTATING SCREW DOSAGE SYSTEM

(71) Applicant: Antares Pharma, Inc., Ewing, NJ (US)

(72) Inventors: Benjamin Newton, Chanhassen, MN (US); Patrick Madsen, Litchfield, MN (US); Matthew Rust, Hudson, WI (US); Janice Cox, St. Paul, MN (US)

(73) Assignee: Antares Pharma, Inc., Ewing, NJ (US)

( * ) Notice: Subject to any disclaimer, the term of this patent is extended or adjusted under 35 U.S.C. 154(b) by 195 days.

This patent is subject to a terminal disclaimer.

(21) Appl. No.: 16/389,627

(22) Filed: Apr. 19, 2019

(65) Prior Publication Data

US 2019/0247586 A1 Aug. 15, 2019

Related U.S. Application Data

(63) Continuation of application No. 14/771,300, filed as application No. PCT/US2014/024543 on Mar. 12, 2014, now Pat. No. 10,300,207.

(Continued)

(51) Int. Cl.
| | | |
|---|---|---|
| *A61M 5/31* | (2006.01) | |
| *A61M 5/315* | (2006.01) | |
| *A61M 5/20* | (2006.01) | |
| *A61M 5/24* | (2006.01) | |
| *G01F 11/02* | (2006.01) | |

(52) U.S. Cl.
CPC .... *A61M 5/31543* (2013.01); *A61M 5/31551* (2013.01); *A61M 5/31585* (2013.01); *A61M 5/31536* (2013.01); *A61M 2005/202* (2013.01); *A61M 2005/2407* (2013.01);
(Continued)

(58) Field of Classification Search
CPC .......... A61M 5/31543; A61M 5/31551; A61M 5/31585; A61M 2005/202; A61M 5/2407; A61M 5/31536; A61M 2005/2407; G01F 11/023; G01F 11/025; G01F 11/027
See application file for complete search history.

(56) References Cited

U.S. PATENT DOCUMENTS

| | | | |
|---|---|---|---|
| 7,695,454 B2 | 4/2010 | Barron et al. | |
| 7,863,259 B1 * | 1/2011 | Sung | A61K 31/55 |
| | | | 514/55 |

(Continued)

*Primary Examiner* — Amber R Stiles
(74) *Attorney, Agent, or Firm* — Morgan, Lewis & Bockius LLP

(57) ABSTRACT

A dispensing mechanism for delivering a dosage of medicament including a housing having a proximal-distal axis; a plunger rod having a screw thread and configured to advance along the proximal-distal axis relative to the housing; a user-operable push button moveable along the proximal-distal axis relative to the housing; a twist driver threadably engaged with the push button such that movement of the push button towards the distal end of the housing causes rotation of the twist driver about the proximal-distal axis; and a driver engaged with the twist driver such that rotation of the twist driver causes rotation of the driver, the driver also engaged with a portion of the plunger rod such that rotation of the driver causes rotation of the plunger rod, advancing the plunger rod along the proximal-distal axis relative to the housing.

17 Claims, 13 Drawing Sheets

Related U.S. Application Data

(60) Provisional application No. 61/779,480, filed on Mar. 13, 2013.

(52) U.S. Cl.
CPC .......... *G01F 11/023* (2013.01); *G01F 11/025* (2013.01); *G01F 11/027* (2013.01)

(56) References Cited

U.S. PATENT DOCUMENTS

| | | | | |
|---|---|---|---|---|
| 2004/0210199 A1* | 10/2004 | Atterbury | ................ | G01D 5/25 604/224 |
| 2009/0247951 A1* | 10/2009 | Kohlbrenner | ........... | A61M 5/24 604/134 |
| 2009/0275916 A1* | 11/2009 | Harms | .............. | A61M 5/31541 604/506 |
| 2010/0036320 A1* | 2/2010 | Cox | ................. | A61M 5/31541 604/135 |
| 2012/0283647 A1* | 11/2012 | Cronenberg | ...... | A61M 5/31551 604/207 |

\* cited by examiner

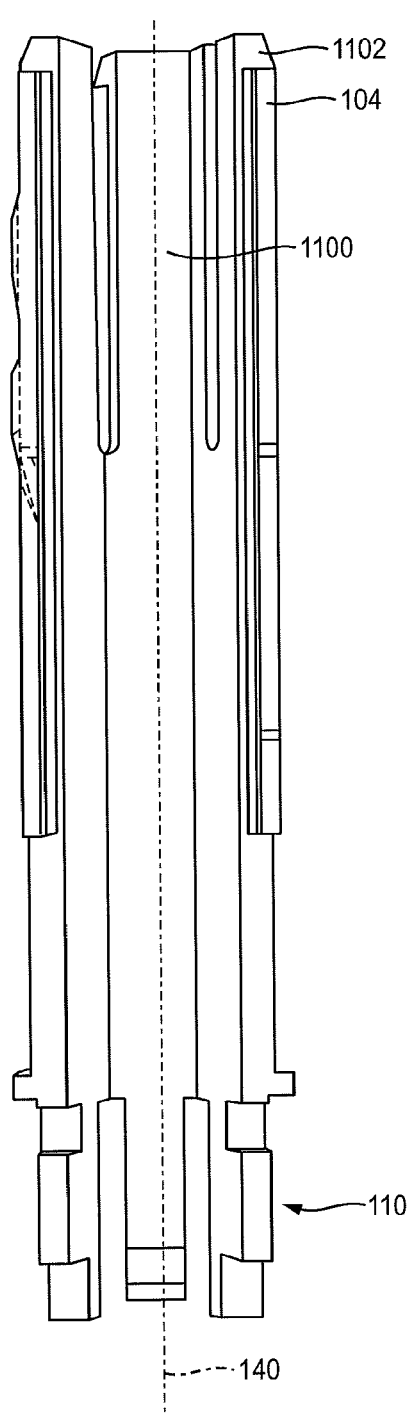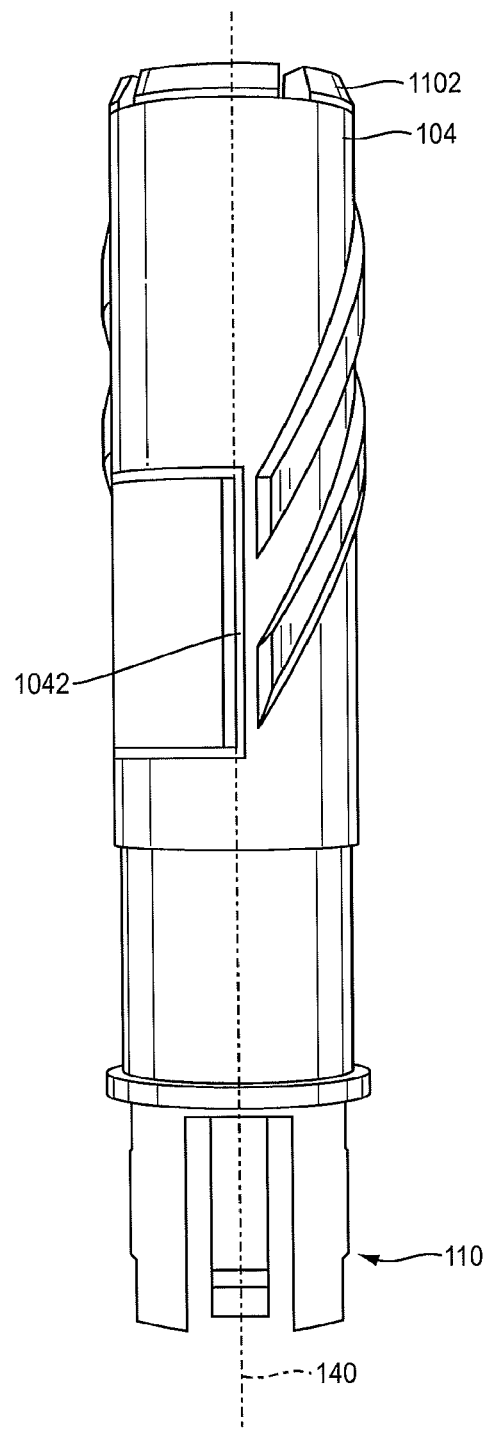
FIG. 7B                    FIG. 7C

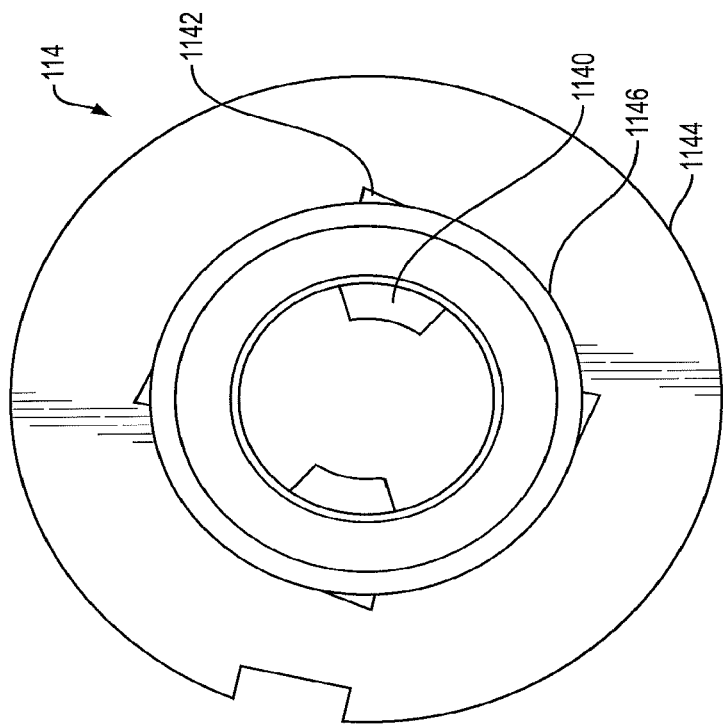
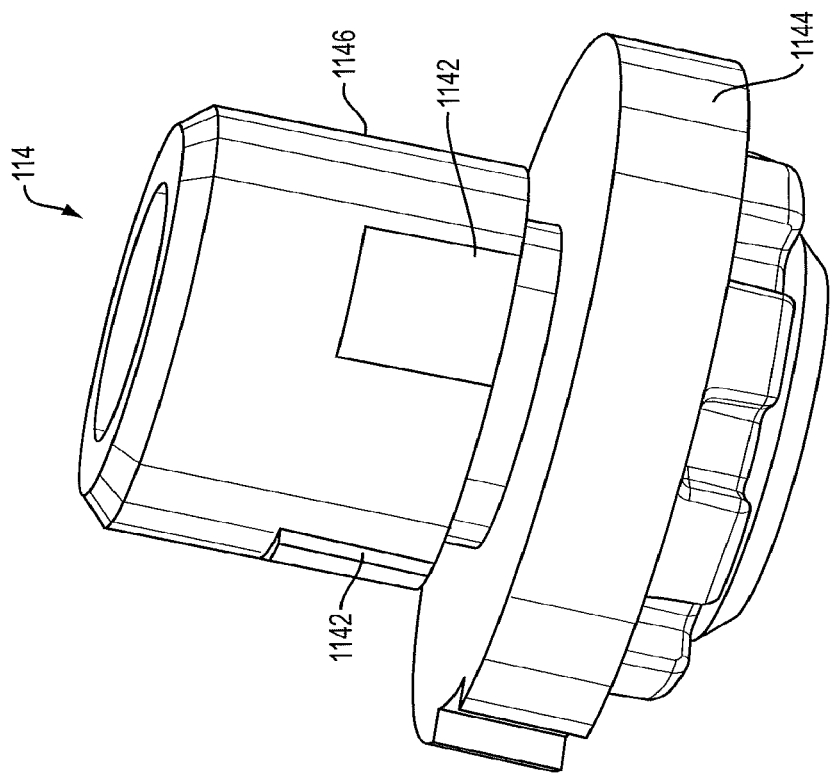
FIG. 9B
FIG. 9A

MULTIPLE DOSAGE INJECTOR WITH ROTATING SCREW DOSAGE SYSTEM

CROSS-REFERENCE TO RELATED APPLICATIONS

This application is a continuation of U.S. patent application Ser. No. 14/771,300 filed Aug. 28, 2015, which in turn is a U.S. National Stage Entry of International Patent Application No. PCT/US2014/024543, filed Mar. 12, 2014, which in turn claims priority of U.S. Provisional Patent Application No. 61/779,480 filed Mar. 13, 2013, which are incorporated by reference herein for all purposes.

FIELD OF THE DISCLOSURE

The present invention relates to an injection device capable of delivering multiple doses of a liquid medicament contained therein without the need to refill the device between doses.

BACKGROUND

Various types of drug treatments, including hormone therapy and the like, require administration of the drug-containing liquid medicament at regular intervals over an extended period of time. For example, a specific hormone treatment can require daily administration of the drug for a period of thirty days. In such a situation, it is advantageous to provide a device that allows the patient to self-administer the injection to avoid repeated trips to a doctor's office or the like.

A device is needed that allows for repeated administration of a dose of medicament that is easy to use correctly in self-administration.

SUMMARY

In one embodiment, the present invention is a dispensing mechanism, including a housing having a proximal-distal axis; a plunger rod having a screw thread and configured to advance along the proximal-distal axis relative to the housing; a user-operable push button moveable along the proximal-distal axis relative to the housing; a twist driver threadably engaged with the push button such that movement of the push button towards the distal end of the housing causes rotation of the twist driver about the proximal-distal axis; and a driver engaged with the twist driver such that rotation of the twist driver causes rotation of the driver, the driver also engaged with a portion of the plunger rod such that rotation of the driver causes rotation of the plunger rod, advancing the plunger rod along the proximal-distal axis relative to the housing.

In one embodiment, the present invention is an injector that includes the dispensing mechanism, a cartridge disposed within the housing; a plunger disposed in the cartridge to seal a medicament therein, wherein the plunger rod is associated with the plunger for forcing the plunger in a distal direction for ejecting a dose of medicament; and a needle in fluid communication with the cartridge for injecting the doses into a patient.

In another embodiment, the medicament includes a parathyroid hormone. In one embodiment, the parathyroid hormone is teriparatide.

In one embodiment, the dispensing mechanism, further includes an anti-reverse mechanism including: at least one ratchet integrally forming on an internal surface of the housing; and a flexible column integrally formed within a side opening of the push button, the flexible column having a flexible column protrusion at a proximal end thereof, wherein as the push button moves along the proximal-distal axis, the flexible column protrusion engages the ratchet and restricts movement of the push button to one direction during a firing motion and a resetting motion. In another embodiment, the flexible column protrusion is generally elliptically shaped.

In one embodiment, the dispensing mechanism further includes a nut fixated within the housing having protrusions on an internal surface that engage the screw thread of plunger rod such that as the plunger rod rotates, the plunger rod is advanced along the proximal-distal axis relative to the housing.

In one embodiment, the twist driver further includes a ratchet flap that is configured to engage a lip of the driver such that the twist driver can axially rotate about the proximal-distal axis in generally only one direction.

In one embodiment, the dispensing mechanism further includes a biasing member disposed within push button to facilitate movement of the push button from a fired position to a reset position.

BRIEF DESCRIPTION OF THE DRAWINGS

These and other objects, features and advantages of the invention will be apparent from a consideration of the following non-limiting detailed description considered in conjunction with the drawing figures, in which:

FIG. 7B is a cross-sectional side view of a driver of the injection device shown in FIG. 1A;

FIG. 7C is a side view of a driver and a twist driver of the injection device shown in FIG. 1A;

FIG. 9A is a perspective view of a nut of the injection device shown in FIG. 1A;

FIG. 9B is a top view of a nut of the injection device shown in FIG. 1A;

Figure 1A:
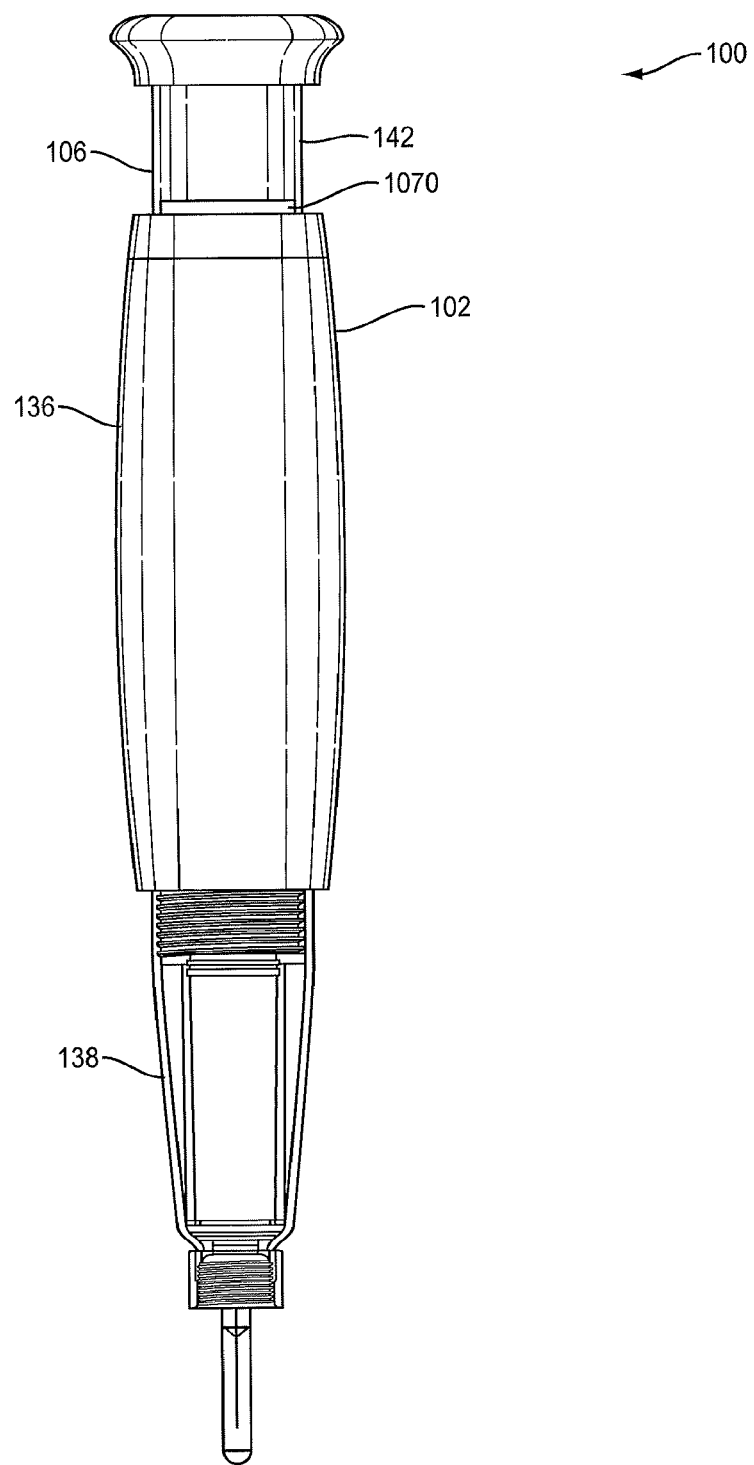
FIG. 1A is a side view of an injection device according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

With reference to the accompanying drawings, various embodiments of the present invention are described more fully below. Some but not all embodiments of the present invention are shown. Indeed, various embodiments of the invention may be embodied in many different form and should not be construed as limited to the embodiments expressly described. Like numbers refer to like elements throughout. The singular forms "a," "an," and "the" include the singular and plural unless the context clearly dictates otherwise.

Referring to the drawings in detail, wherein like reference numerals indicate like elements throughout, there is shown in FIGS. 1-11 an injection device 100, in accordance with an exemplary embodiment of the present invention. It is noted that, in the context of this disclosure, the terms "distal" and "proximal" are used in reference to the position of injection device 100 relative to a user of the injection device when held by a user. Accordingly, a point located distal to a second point would be further from the user (e.g., towards an injection end of injection device 100) and vice versa.

Figure 1B:
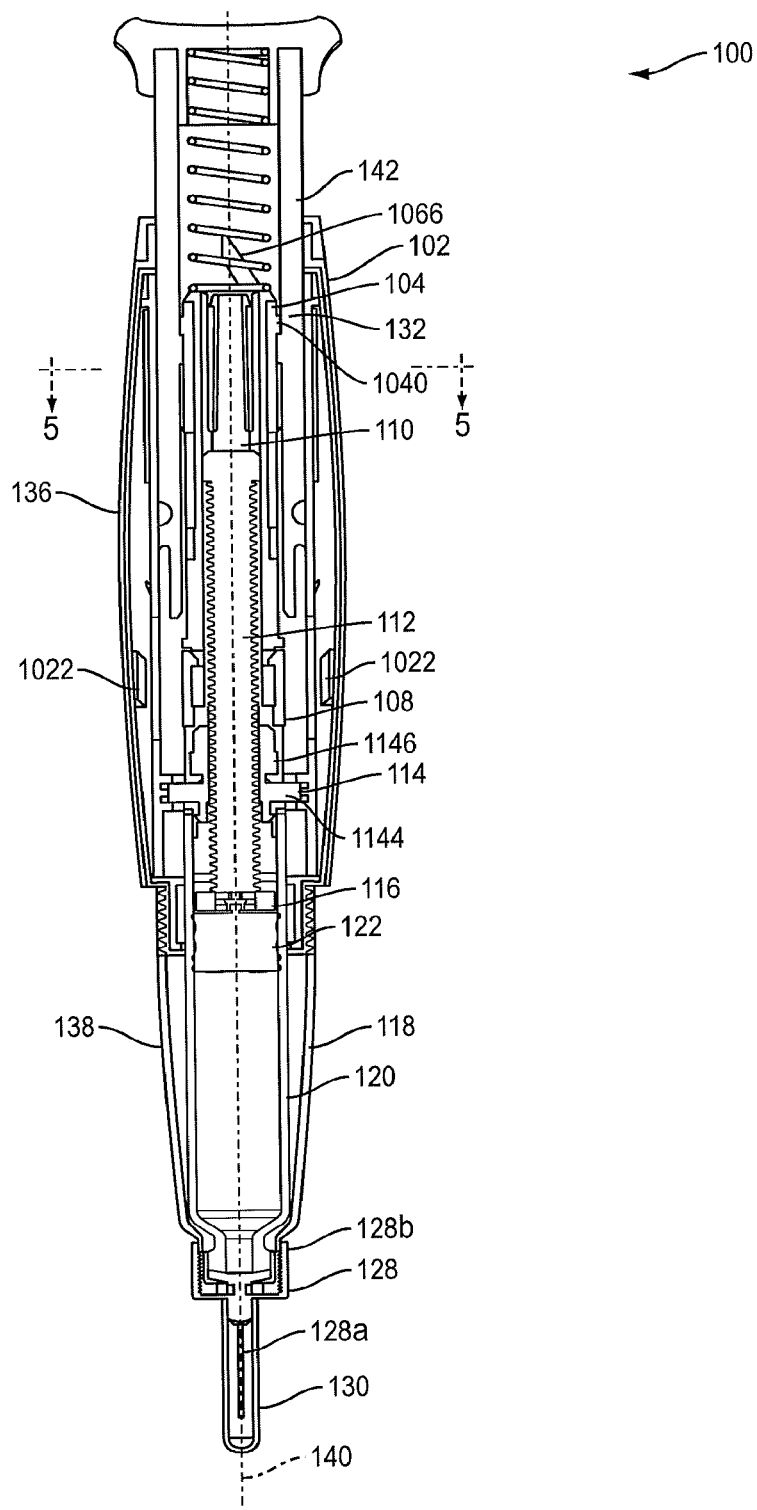
FIG. 1B is a cross-sectional side view of the injection device shown in FIG. 1A.

Referring to FIGS. 1A and 1B, in one embodiment, injection device 100 is configured to administer a dose of medicament. In one embodiment, injection device 100 is configured in the shape of a pen, having an elongated, substantially writing instrument-like form, although other forms are within the scope of the invention. In one embodiment, injection device 100 is a disposable pen, in that after the quantity of medicament contained therein is exhausted by multiple operations of the injection device 100, the injection device 100 is discarded rather than being reset and related with a replacement container of medicament. In other embodiments, injection device 100 can be reset and is reusable.

In one embodiment, injection device 100 is configured to administer repeated, successive doses of a medicament. In one embodiment, the medicament is delivered in successive repeated fixed doses. In one embodiment, the medicament is delivered in successive repeated variable doses. In other embodiments, the dosage can be controlled and adjusted. Further, in one embodiment, injection device 100 allows the injection to be administered by individuals that do not have formal training (e.g., self-administered or administered by another individual family member or other caregiver who may not be a formally trained healthcare provider, such as a parent administering a drug to a child). In one embodiment, injection device 100 is triggered by one hand of a user. In one embodiment, injection device 100 is held one in hand of a user and triggered by the user's thumb. In one embodiment, injection device 100 is useful in situations where self-injections/caregiver administered injections would be beneficial, including, but not limited to, the injection of a drug to treat osteoporosis. In one embodiment, the injection device must administer a full dose prior to being able to reset. In one embodiment, the injection device must fully reset before it is able to be fired.

The injection device 100 can be used to inject a wide range of drugs. For example, injection device 100 can be used to inject drugs, water soluble medicaments and oil soluble medicaments. Some medicaments that can be used with the injector device 100 include parathyroid hormone ("PTH") and various other medications such as exenatide and the like. Injection device 100 can also be used to inject medicaments listed in the Physicians' Desk Reference (PDR®), 67th Edition (2013) (which is herein incorporated by reference in its entirety), and, without limitation, allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antibiotics, antiviral antibiotics, anticancer preparations, anticholinergic drug inhibitors, anticoagulants, anticonvulsants, antidepressants, antidiabetic agents, antidiarrheals, antidiuretics, antienuresis agents, antifibrinolytic agents, antifibrotics (systemic), antiflatulents, antifungal agents, antigonadotropin, antihistamines, antihyperammonia agents, anti-inflammatory agents, antimalarials, antimetabolites, antimigraine preparations, antinauseants, antineoplastics, anti-obesity preparations, antiparasitics, antiparkinsonism drugs, antipruritics, antipyretics, antispasmodics and antichloinergics, antitoxoplasmosis agents, antitussives, antivertigo agents, antiviral agents, apomorphine, atropine, biologicals, biosimilars, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, cough and cold preparations, decongestants, diazepam, dihydroergotamine, epinephrine expectorants and combinations, diuretics, emetics, enzymes and digestants, fertility agents, fluorine preparations, galactokinetic agents, general anesthetic, geriatrics, germicides, glucagon, haloperidol, hematinics, hemorrhoidal preparations, histamine H receptor antagonists, hormones, hydrocholeretics, hyperglycemic agents, hypnotics, immunosuppressives, laxatives, lovenox, mucolytics, muscle relaxants, narcotic antagonists, narcotic detoxification agents, ophthalmological osmotic dehydrating agents, otic preparations, oxytocics, parashypatholytics, parathyroid preparations, pediculicides, peptide drugs, phosphorus preparations, premenstrual therapeutics, psychostimulants, quinidines, radiopharmaceuticals, respiratory stimulants, salt substitutes, scabicides, sclerosing agents, sedatives, sumatriptan, sympatholytics, sympathomimetics, thrombolytics, thyroid preparations, toradol, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the PDR®. Some other medicaments that can be used with injector device 100 include Ergocalciferol (Calciferol), diethylstilbestrol, Diprovan (propofol), estradiol valerate, fluphenazine decanoate, fulvestrant, intralipid, liposyn, nandrolone decanoate, nebi do, nutralipid, paclitaxel, progesterone, prograf, testosterone cypionate, zuclopenthixol, haloperidol dodecanoate, Enbrel, Humira, Lantus, Epogen (Procrit), Neulasta, Aranesp, Avonex, PEGasys, Rebif, Neupogen, Betaseron, Avastin, Remicade, Herceptin, Erbitux, Recombinate, Cerezyme, Novo Seven, Tysabri, Synagis, Copaxone and Kogenate FS. In certain embodiments, the medicament is dissolved in soybean oil, ethyl oleate, castor oil, sesame oil, safflower oil, arachis oil, polyoxyyethylated castor oil (Cremophor® EL), polyoxyl 60 hydrogenated castor oil (HCO-60), cottonseed oil, or thin oil derived from coconut oil.

In some embodiments, the medicament may be a hazardous agent. "Hazardous Agent(s)" as used herein means any one or more medications that are toxic agents, cytotoxic agents and/or other dangerous agents that may cause serious effects upon contact with a subject as well as highly potent agents, agents that have profound physiological effects at low doses. Exemplary hazardous agents include, without limitation, analgesics, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. Examples of hazardous agents suitable for use with the injection device 100 in accordance with the present invention include, but are not limited to, those disclosed in U.S. Patent Application Publication No. 2012/0157965 entitled "Hazardous Agent Injection System" (to Paul Wotton et. al, published Jun. 21, 2012), which is incorporated by reference herein in its entirety. Particular examples of cytotoxic agents include, without limitation, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, and derivatives thereof. Examples of highly potent agents include, without limitation, steroids such as dexamethasone, progesterone, somatostatin, and analogues thereof; biologically active peptides such as teriparatide; and anticholinergics such as scopolamine. Examples of agents that have profound physiological effects at low doses include, without limitation, antihypertensives and/or blood pressure down regulators. Examples of analgesics include, without limitation, fentanyl, fentanyl citrate, morphine, meperidine, and other opioids. Examples of immunomodulating agents include, without limitation, adalimumab (anti-tissue necrosis factor monoclonal antibody or anti-TNF). Examples of IL-1 receptor antagonists include, without limitation, anakinra. Examples of IL-2 alpha receptor antagonists include, without limitation, daclizumab and basiliximab. Examples of anti-rejection compounds include, without limitation, azathioprine, cyclosporine, and tacrolimus. Examples of hormonal agents include, without limitation, testosterone, estrogen, growth hormone, insulin, thyroid hormone, follicle stimulating hoimone (FSH), epinephrine/adrenaline, progesterone, parathyroid hormone, gonadotrophin releasing hormone (GHRH), leutinizing hormone releasing hormone (LHRH), other hormones such as those where contact with the hormone by members of the opposite sex can lead to side effects, and derivatives thereof. Examples of prostaglandins include, without limitation, gamma-linolenic acid, docosahexanoic acid, arachidonic acid and eicosapentaenoic acid. Examples of sedatives include, without limitation, barbiturates such as amobarbital, pentobarbital, secobarbital, and phenobarbitol; benzodiazepines such as clonazepam, diazepam, estazolam, flunitrazepam, lorazepam, midazolam, nitrazepam, oxazepam, triazolam, temazepam, chlordiazepoxide, and alprazolam; herbal sedatives such as ashwagandha, *duboisia hopwoodii*, prosanthera striatiflora, kava (*piper methysticum*), mandrake, valerian, and marijuana; non-benzodiazepine sedatives (a.k.a. "Z-drugs") such as eszopiclone, zaleplon, zolpidem, zopiclone; antihistamines such as diphenhydramine, dimenhydrinate, doxylamine, and promethazine; and other sedatives such as chloral hydrate. Examples of anticholinergic agents include, without limitation, dicyclomine, atropine, ipratropium bromide, oxitropium bromide, and tiotropium. Examples of Parkinson's disease drugs include, without limitation, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, and lisuride. Examples of expensive agents include, without limitation, human growth hormone and erythropoietin. Examples of neuroleptic agents includes, without limitation, antipsychotics; butyrophenones such as haloperidol and droperidol; phenothiazines such as chlorpromazine, fluphenazine, perphenazine, prochlorperazine, thioridazine, trifluoperazine, mesoridazine, periciazine, promazine, triflupromazine, levomepromazine, promethazine, and pimozide; thioxanthenes such as chlorprothixene, clopenthixol, flupenthixol, thiothixene, and zuclopenthixol; atypical antipsychotics such as clozapine, olanzapine, risperidone, quetiapine, ziprasidone, amisulpride, asenapine, paliperidone, iloperidone, zotepine, and sertindole; and third generation antipsychotics such as aripiprazole and bifeprunox. Examples of TNF blockers includes, without limitation, etanercept.

In some embodiments, the hazardous agent can be selected from botulinum toxin, injectable gold, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, dexamethasone, progesterone, somatostatin, analogues of dexamethasone, analogues of progesterone, analogues of somatostatin, teriparatide, scopolamine, antihypertensives, blood pressure down regulators, fentanyl, fentanyl citrate, morphine, meperidine, other opioids, adalimumab (anti-tissue necrosis factor monoclonal antibody or anti-TNF), anakinra, daclizumab, basiliximab, azathioprine, cyclosporine, tacrolimus, testosterone, estrogen, growth hormone, insulin, thyroid hormone, follicle stimulating hormone (FSH), epinephrine/adrenaline, gamma-linolenic acid, docosahexanoic acid, arachidonic acid, eicosapentaenoic acid, amobarbital, pentobarbital, secobarbital, phenobarbitol, clonazepam, diazepam, estazolam, flunitrazepam, lorazepam, midazolam, nitrazepam, oxazepam, triazolam, temazepam, chlordiazepoxide, alprazolam, ashwagandha, *duboisia hopwoodii*, prosanthera striatiflora, kava (*piper methysticum*), mandrake, valerian, marijuana, cszopiclone, zaleplon, zolpidem, zopiclone, diphenhydramine, dimenhydrinate, doxylamine, promethazine, chloral hydrate, dicyclomine, atropine, ipratropium bromide, oxitropium bromide, tiotropium, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, lisuride, human growth hormone, erythropoietin, haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, etanercept, derivatives of any of the foregoing, and combinations of any of the foregoing.

Because of the repeated nature of the dosing of certain types of medicaments, it is beneficial to use a device that aides a patient in self-administration of the doses. Further, many such medicaments should be delivered in a precise amount to ensure efficacy and to reduce side-effects.

In one embodiment, the medicament includes a recombinant form of parathyroid hormone, e.g., teriparatide. Teriparatide has the following structure:

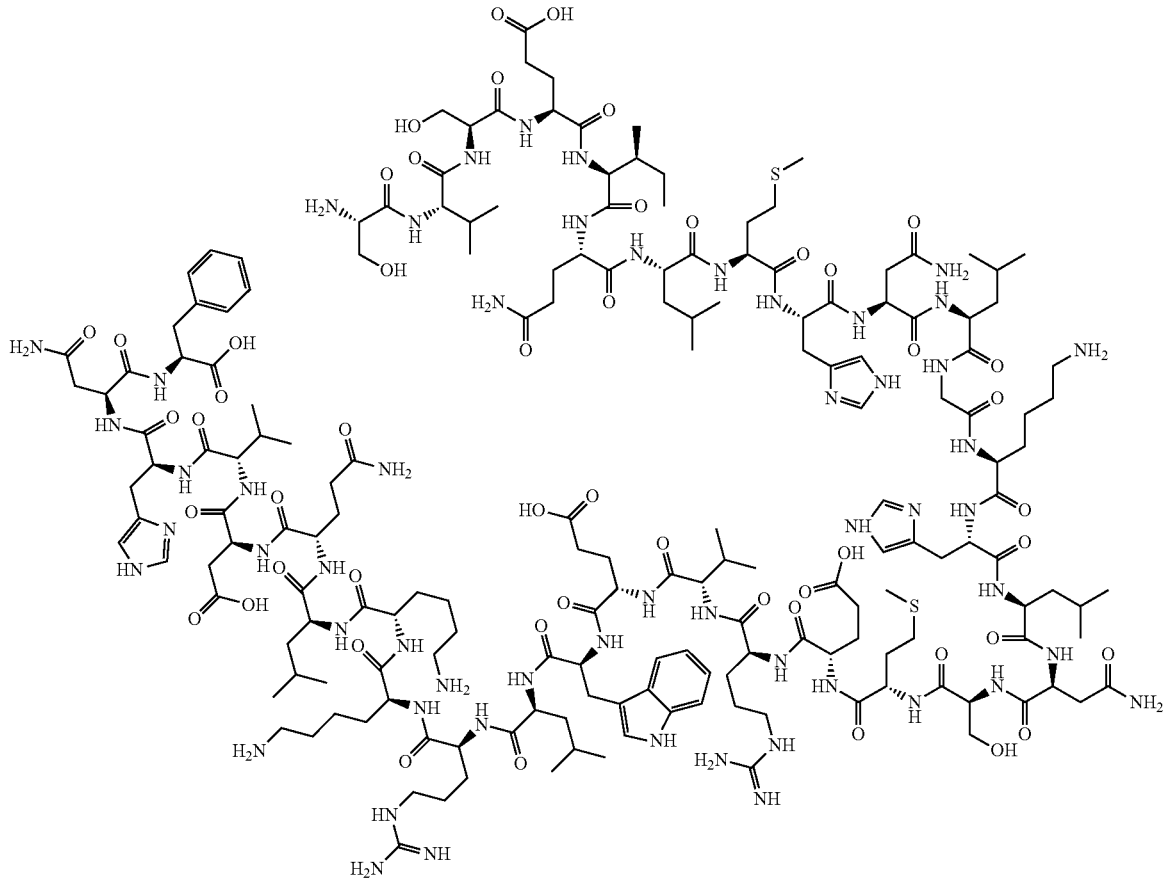

Teriparatide is typically administered by injection once a day in the thigh or abdomen. Teriparatide is indicated for use in postmenopausal women with osteoporosis at a high risk for fracture or with a history of ostoporotic fracture, patients with multiple risk factors for fracture, and for patients who have failed or are intolerant to other available osteoporosis therapy. Teriparatide is also indicated to increase bone mass in men with primary or hypogonadal osteoporosis at high risk of fracture, patients with multiple risk factors for fracture, and for patients who have failed or are intolerant to other available osteoporosis therapy. Teriparatide is indicated as well for the treatment of men and women with osteoporosis associated with sustained systemic glucocorticoid therapy. The typical recommended dose is 20 µg per day. In one embodiment, injection device 100 is configured to administer about 1 µg, about 2 µg, about 3 µg, about 4 µg, about 5 µg, about 6 µg, about 7 µg, about 8 µg, about 9 µg, about 10 µg, about 11 µg, about 12 µg, about 13 µg, about 14 µg, 15 µg, about 16 µg, about 17 about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, about 40 µg or any range determinable from the preceding dosage amounts (for example, about 15 µg to about 25 µg or about 1 µg to about 10 µg) of medicament, e.g., Teriparatide, per dose. In one embodiment, injection device 100 is configured to administer about 0.005 mL, about 0.010 mL, about 0.015 mL, about 0.020 mL, about 0.025 mL, about 0.030 mL, about 0.035 mL, about 0.040 mL, about 0.045 mL, about 0.050 mL, about 0.055 mL, about 0.060 mL, about 0.065 mL, about 0.070 mL, 75 about 0.080 mL, about 0.085 mL, about 0.090 mL, about 0.095 mL, about 0.100 mL, about 0.105 mL, about 0.110 mL, about 0.115 mL, about 0.120 mL, about 0.125 mL, about 0.130 mL or any range determinable from the preceding dosage amounts (for example, about 0.025 mL to about 0.045 mL or about 0.005 mL to about 0.130 mL) of medicament, e.g., Teriparatide, per dose.

Referring to FIG. 1B, in one embodiment, injection device 100 includes a proximal section 136 and a distal section 138. In one embodiment, distal section 138 contains the medicament to be dispensed at its distal end upon operation of injection device 100. In one embodiment, the proximal section 136 contains the dosage mechanism 132 used to force the contained medicament from the distal end of distal section 138.

In one embodiment, injection device 100 includes housing 102. In one embodiment, housing 102 has a proximal-distal axis 140. In one embodiment, housing 102 of injection device 100 is formed from a light weight material, e.g., an injected molded plastic. In one embodiment, housing 102 is formed of at least two separate parts. In one embodiment, the at least two housing parts are aligned via mating pins and recesses provided therein and fixedly secured together during manufacture, such as via adhesives or ultrasonic welding. In one embodiment, housing 102 is generally bulbous shaped to accommodate dosage mechanism 132. In one embodiment, housing 102 is provided with an external thread at a distal portion of the housing 102 or another suitable connections means to releasably connect a cartridge sleeve 118 thereto.

In one embodiment, distal section 138 of injection device 100 includes a cartridge sleeve 118 which can be used to hold a number of differently-sized cartridges. Additionally, a number of differently-sized cartridge sleeves can be provided, as necessary for differently-sized cartridges. In one embodiment, the cartridge sleeve 118 is provided with an internal thread or another suitable connections means at a proximal portion of the cartridge sleeve 118 to releasably connect housing 102 thereto. In one embodiment, the cartridge sleeve 118 is provided with an external thread or another suitable connections means at a distal portion of cartridge sleeve 118 to releasably connect a removable cap (not shown). In one embodiment, the cartridge sleeve 118 is provided with an external thread or another suitable connections means at a distal portion of cartridge sleeve 118 to releasably connect a pen-needle assembly 128 thereto.

In one embodiment, a pen-needle assembly 128 is of known design and includes a double-ended needle cannula or injection needle 128a. In one embodiment, an injection needle 128a is mounted in a tubular hub 128b that is internally threaded to cooperate with the external thread of cartridge sleeve 118 so as to be screwable onto and off of the external threading of the cartridge sleeve 118. Other types of connection types, including a snap on connection, may be provided between pen-needle assembly 128 and cartridge sleeve 118. In one embodiment, injection needle 128a is fitted with a protective cover, e.g., a needle cap 130, thereover to protect those handling or who may otherwise encounter injection device 100. In one embodiment, pen-needle assembly 128 includes a single injection needle. Various types of other needle assemblies known in the art may be used with injection device 100, including, but not limited to, assemblies with one or more shortened injection needles, including microneedle arrays, or assemblies having intravenous lines or the like.

In one embodiment, injection device 100 includes a cartridge 120. In one embodiment, cartridge 120 is of the type typically used in connection with injection devices, e.g., needled injector devices, and is formed of glass or certain types of plastic that have qualities that are necessary for storage of liquid medicament. Such qualities can include low air permeation, lubricity, low leeching of chemicals and corrosion resistance. In one embodiment, cartridge 120 is generally cylindrical in shape and can have a diameter configured to fit within cartridge sleeve 118, although other shapes can be used. In one embodiment, cartridge 120 and cartridge sleeve 118 are engaged at an interface. In one embodiment, a light cure adhesive is applied at the interface of cartridge 120 and cartridge sleeve 118. In one embodiment, cartridge 120 defines a medicament-filled reservoir that is closed at its proximal end by a plunger 122 that is axially slideably and sealably engaged with the cartridge interior wall to hold the medicament within the reservoir. In one embodiment, the distal, outlet end of the cartridge reservoir is sealed by a septum held by a cap that is secured to a stepped-down diameter neck portion of cartridge 120. In one embodiment, when pen-needle assembly 128 is mounted on cartridge sleeve 118, a proximal point of injection needle 128a penetrates the cartridge septum to provide a fluid flow outlet by which medicament within the cartridge reservoir can be dispensed from a needle tip during operations of injection device 100. In one embodiment, cartridge 120 is configured to contain a predetermined amount of a medicament. The predetermined amount of medicament that cartridge 120 is configured to contain can vary with the medicament injected and with the recommended dose size for the particular medicament and the patient. In one embodiment, distally advancing plunger 122 causes the volume of the cartridge reservoir to decrease and an amount of liquid medicament to expel from injection needle 128a in an amount that corresponds to the reduction in volume caused by the movement of the plunger.

To reliably provide repeated small doses of a liquid medicament, in one embodiment, cartridge 120 is constructed to hold a predetermined number of doses. In one embodiment, the doses in cartridge 120 correspond to a predetermined period of medicament administration. For example, in one embodiment, injector device 100 is intended for use with a teriparatide solution that is to be administered once daily for thirty successive days at a dose of about 0.08 mL administered through movement of a plunger 122 a distance of about 1.1 mm. In one embodiment, the injector device 100 is configured to administer a dose of medicament, e.g., teriparatide, once daily for 1 day, 2 successive days, 3 successive days, 4 successive days, 5 successive days, 6 successive days, 7 successive days, 8 successive days, 9 successive days, 10 successive days, 11 successive days, 12 successive days, 13 successive days, 14 successive days, 15 successive days, 16 successive days, 17 successive days, 18 successive days, 19 successive days, 20 successive days, 21 successive days, 22 successive days, 23 successive days, 24 successive days, 25 successive days, 26 successive days, 27 successive days, 28 successive days, 29 successive days, 30 successive days, 31 successive days, 32 successive days, 33 successive days, 34 successive days, 35 successive days, 36 successive days, 37 successive days, 38 successive days, 39 successive days, 40 successive days, or any range determinable from the preceding days (for example, 3 successive days to 5 successive days or 25 successive days to 35 successive days).

In one embodiment, cartridge 120 is configured to contain about 3 mL of teriparatide. In an embodiment, cartridge 120 has a diameter of about 12 mm and a height of approximately 64 mm to contain 3 mL of medicament, although other dimensions can be used to achieve the desired accuracy. Cartridges 120 containing more or less medicament can be provided and can vary in diameter, height or both. In one embodiment, cartridge 120 is configured to hold between about 0.5 mL, 1.0 mL, about 1.5 mL, about 2.0 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.0 mL, about 9.5 mL, about 10.0 mL or any range determinable from the preceding amounts (for example, about 2 mL to about 5 mL or about 3.0 mL to about 9.5 mL) of liquid medicament. In one embodiment, injection device 100 is configured to dispense different amounts of liquid medicament per dose. Further, the overall volume can be increased to include a predetermined amount of additional volume that remains in cartridge 120 when the intended dosing is complete. This can reduce the likelihood of an incomplete final dose or the presence of air in an injection.

Referring to FIG. 1B, proximal section 136 contains the dosage mechanism 132 which is configured to cause movement of plunger 122 a predetermined dosing distance in a number of successive increments that correspond to the number of doses to be administered. With additional reference to FIGS. 2A and 2B, in one embodiment, dosage mechanism 132 includes a user-manipulable push button 142, a twist driver 104, a driver 110, a plunger rod 112, a driver clip 108, and a nut 114.

Figure 2A:
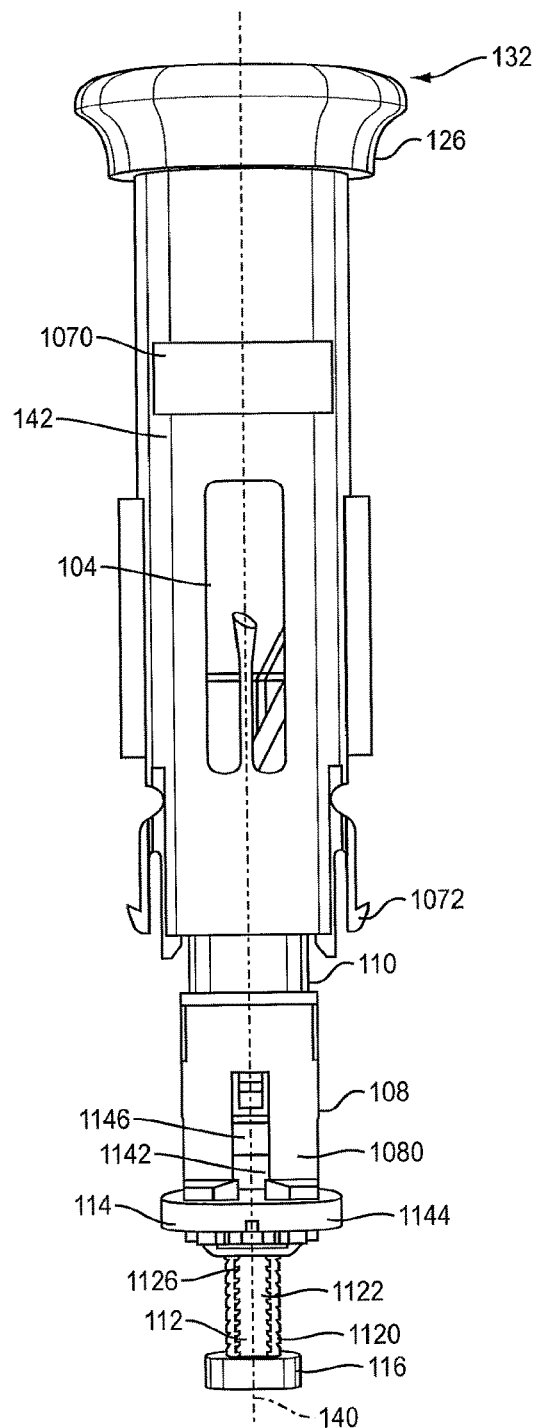
FIG. 2A is a side view of a dosage mechanism of the injection device shown in FIG. 1A.
Figure 3A:
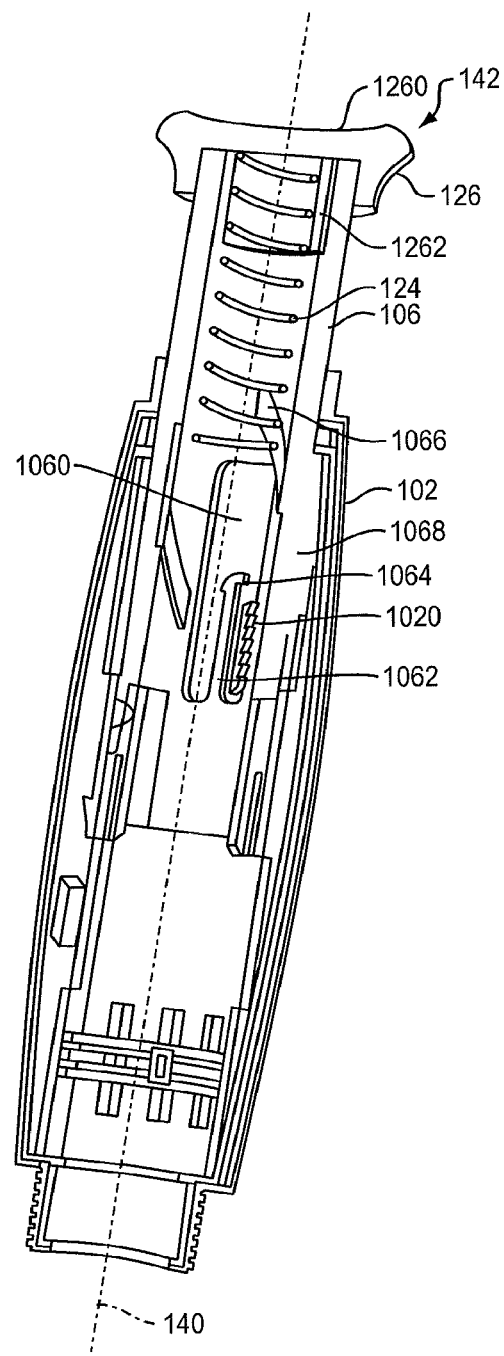
FIG. 3A is a cross-sectional side view of a push button and housing of the injection device shown in FIG. 1A.
Figure 3B:
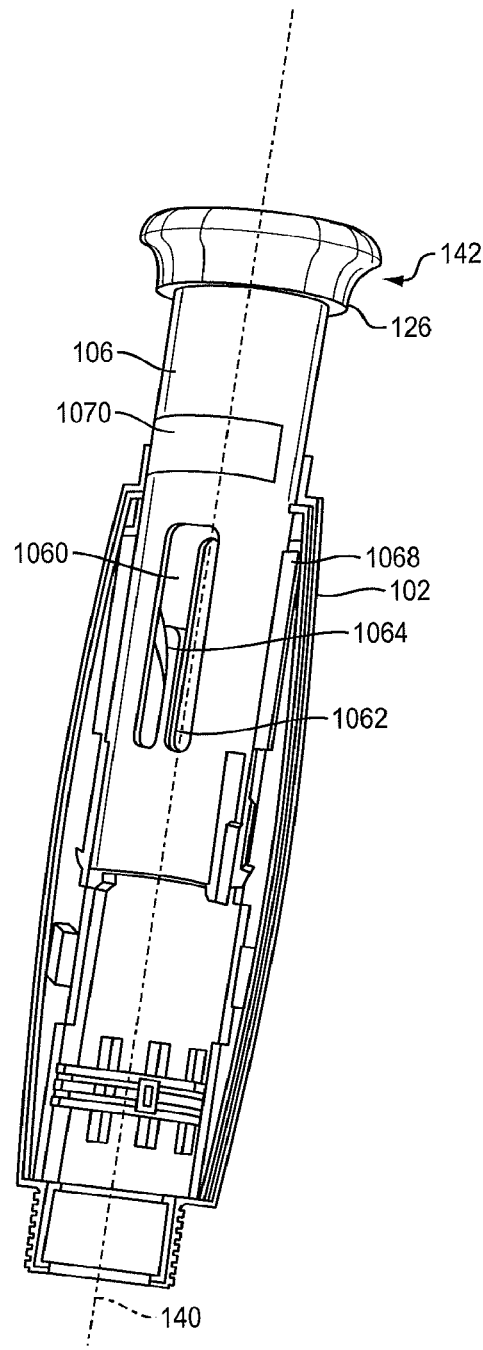
FIG. 3B is a side view of a push button and a portion of housing of the injection device shown in FIG. 1A.

Referring to FIG. 2A, in one embodiment, dosage mechanism 132 includes a user-manipulable push button 142 that allows the user to actuate the injection device 100. With further reference to FIGS. 3A and 3B, in one embodiment, push button 142 includes a trigger member 106, a cap 126, and a force limiting biasing member 124.

In one embodiment, trigger member 106 is sized and shaped to be slideably engageable with housing 102. In one embodiment, trigger member 106 is generally cylindrically shaped. In another embodiment, trigger member 106 includes protrusions 1068 which are configured to slideably engage slots of housing 102 to restrict movement of push button 142 to linear movements along axis 140. Alternatively, in one embodiment, trigger member 106 includes slots which are configured to slideably engage protrusions of housing 102 to restrict movement of push button 142 to linear movements along axis 140.

Figure 2B:
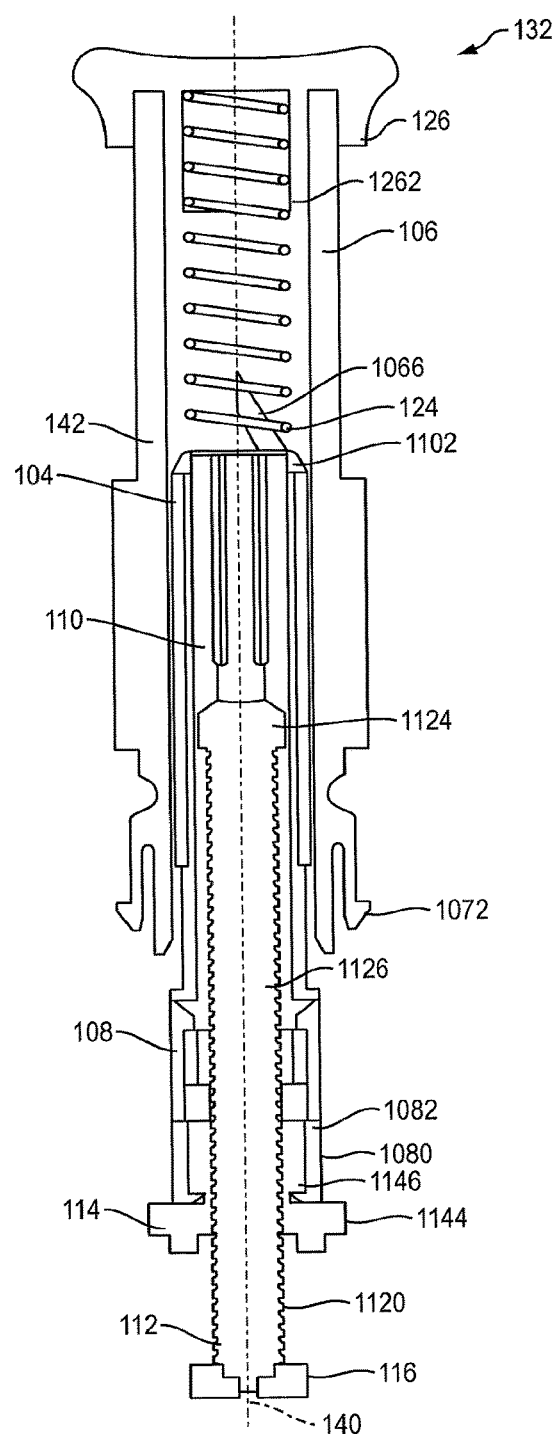
FIG. 2B is a cross-sectional side view of the dosage mechanism of the injection device shown in FIG. 1A.

In one embodiment, trigger member 106 includes threads 1066 disposed on the interior surface of the trigger member 106. As shown in FIG. 2B, in one embodiment, threads 1066 are configured to allow slideable engagement of trigger member 106 with a twist driver 104 (described in more detail below).

Referring to FIG. 1A, in one embodiment, trigger member 106 includes an indicating band 1070 on its outer surface. In one embodiment, indicating band 1070 is configured to be visible to a user when push button 142 has been properly withdrawn from the housing 102 to prepare injection device 100 for medicament delivery. In one embodiment, indicating band 1070 extends continuously along the circumference of trigger member 106. In other embodiments, indicating band 1070 extends discontinuously along the circumference of trigger member 106. In one embodiment, indicating band 1070 can incorporate a color, e.g., red, to add to the affect thereof. In one embodiment, when indicating band 1070 is visible, injection device 100 is in a ready (or reset) state. In one embodiment, when injecting band 1070 is not visible, injection device 100 is in a fired state.

In one embodiment, movement of push button 142 distally along axis 140 from a ready (or reset) state towards a fired state is considered firing motion. Whereas, in another embodiment, movement of push button 142 proximally along axis 140 from a fired state towards a ready (or reset) state is considered resetting motion.

Figure 4:
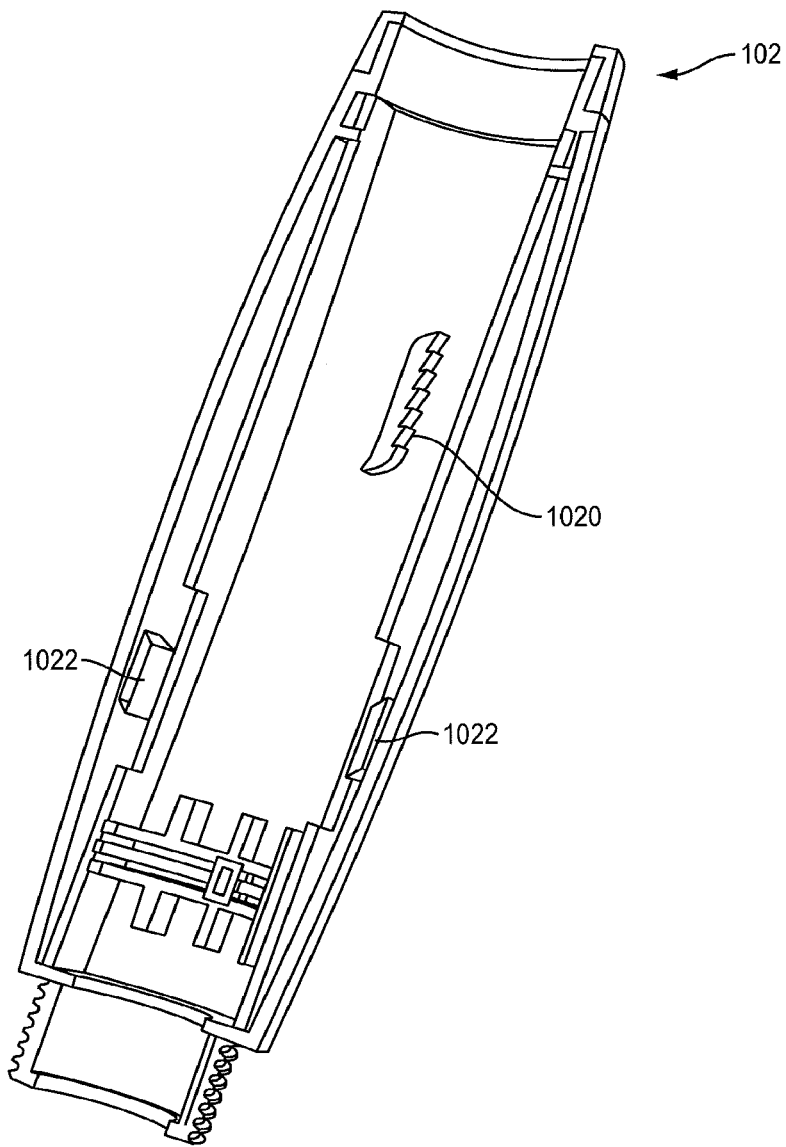
FIG. 4 is a side view of a portion of housing of the injection device shown in FIG. 1A.

Referring to FIGS. 3A and 3B, in one embodiment, trigger member 106 includes at least one aperture 1060 disposed through the surface of trigger member 106. In another embodiment, trigger member 106 includes at least two apertures 1060 disposed through the surface of trigger member 106. In one embodiment, trigger member 106 includes at least two diametrically opposed apertures 1060 disposed through the surface of trigger member 106. In one embodiment, each aperture 1060 includes a flexible column 1062 extending proximally from a distal portion of aperture 1060. In other embodiments, a protrusion 1064 extends perpendicularly from a proximal portion of each flexible column 1062. In certain embodiments, protrusions 1064 are generally almond shaped. In other embodiments, protrusions 1064 are generally cylindrically shaped. In other embodiments, protrusions 1064 are generally polyhedronally shaped. Other shapes of protrusions 1064 are within the scope of this invention. In one embodiment, protrusions 1064 are configured to engage a ratchet 1020, which is integrally formed on the internal surface of housing 102. FIG. 4 shows an exemplary embodiment of housing 102. In one embodiment, there are at least two ratchets 1020 integrally formed on the internal surface of housing 102.

Referring to FIGS. 3A and 4, in one embodiment, ratchets 1020 have a smooth linear side and ratcheted side. In one embodiment, the ratcheted side of ratchets 1020 are configured to engage protrusions 1064 and only allow movement of push button 142 in one direction, e.g., from the fired state to the ready (or reset) state. In certain embodiments, ratchets 120 have curved surfaces at both a proximal end and a distal end. In one embodiment, the proximal curved surface of ratchets 1020 are configured to bias flexible columns 1062 in a way to force protrusions 1064 to the smooth linear side of ratchets 102. In one embodiment, the distal curved surface of ratchets 1020 are configured to bias flexible columns 1062 in a way to force protrusions 1064 to the ratcheted sides of ratchets 1020. In one embodiment, during resetting motion of push button 142, protrusions 1064 engage the distal curved surfaces of ratchets 1020, causing flexible columns 1062 to bias and forcing protrusions 1064 to the ratcheted side of ratchets 1020. In certain embodiments, if push button 142 is moved in a distal direction prior to completion of the resetting motion, protrusions 1064 would engage the ratchets of ratchets 1020, preventing distal movement of push button 142. In one embodiment, during firing motion of push button 142, protrusions 1064 engage the proximal curved surfaces of ratchets 1020, causing flexible columns 1062 to bias and forcing protrusions 1064 to the smooth linear side of ratchets 1020. In certain embodiments, protrusions 1064 slide along the smooth linear side of ratchets 1020 until the device is in the fired state. In one embodiment, the full amount of medicament which is to be expelled during the firing motion is only fully expelled upon push button 142 reaching the fired state. In one embodiment, if push button 142 does not complete the firing motion, the full amount of medicament for that dose is not fully expelled. In certain embodiments, a successive dose cannot be effectuated until the previous dosage amount of medicament is fully expelled. In one embodiment, the combination of flexible columns 1062, protrusions 1064 and ratchets 1020 are considered an anti-reverse feature.

Referring to FIGS. 3A and 3B, in one embodiment, push button 142 includes cap 126. In one embodiment, cap 126 includes a user-contacting portion 1260 and tabs 1262. In one embodiment, cap 126 has a hollow portion configured to fit force limiting biasing member 124. In one embodiment, cap 126 is molded from plastic. In other embodiments, cap 126 is covered with a soft touch material. In one embodiment, cap 126 is fixed to trigger member 106. In one embodiment, tabs 1262 are sized and shaped to fix cap 126 to trigger member 106. Other fixation means are within the scope of this invention.

Referring to FIG. 2B, in one embodiment, force limiting biasing member 124 of push button 142 is a metal, helically-coiled compression spring. In one embodiment, force limiting biasing member 124 is disposed within a hollow portion of cap 126. In one embodiment, force limiting biasing member 124 is captured in a pre-stressed state between the interior end of cap 126 and a top portion of flanges 1102 of driver 110 (described in more detail below). In one embodiment, the pre-stressing is at least as large as forces the manufacturer expects users to apply on the plunger button during normal plunging to achieve proper operation of injection device 100. In one embodiment, in which a mechanical advantage (as discussed further below)

of nominally about ten to one is provided by the apparatus, the pre-stressing is in an amount of one pound per square inch. Thus, in one embodiment, during normal actuation of injection device 100, force limiting biasing member 124 does not further compress. In another embodiment, force limiting biasing member 124 is designed with sufficient spacing in its coiling, and with proper elastic properties, such that the force limiting biasing member 124, by compression, can accommodate movement of push button 142 from a ready (or reset) state to a fired stated without movement of twist driver 104, plunger rod 112, driver 110, or driver clip 108 whereby force limiting biasing member 124 can absorb actuation forces that could damage these components.

Figure 5:
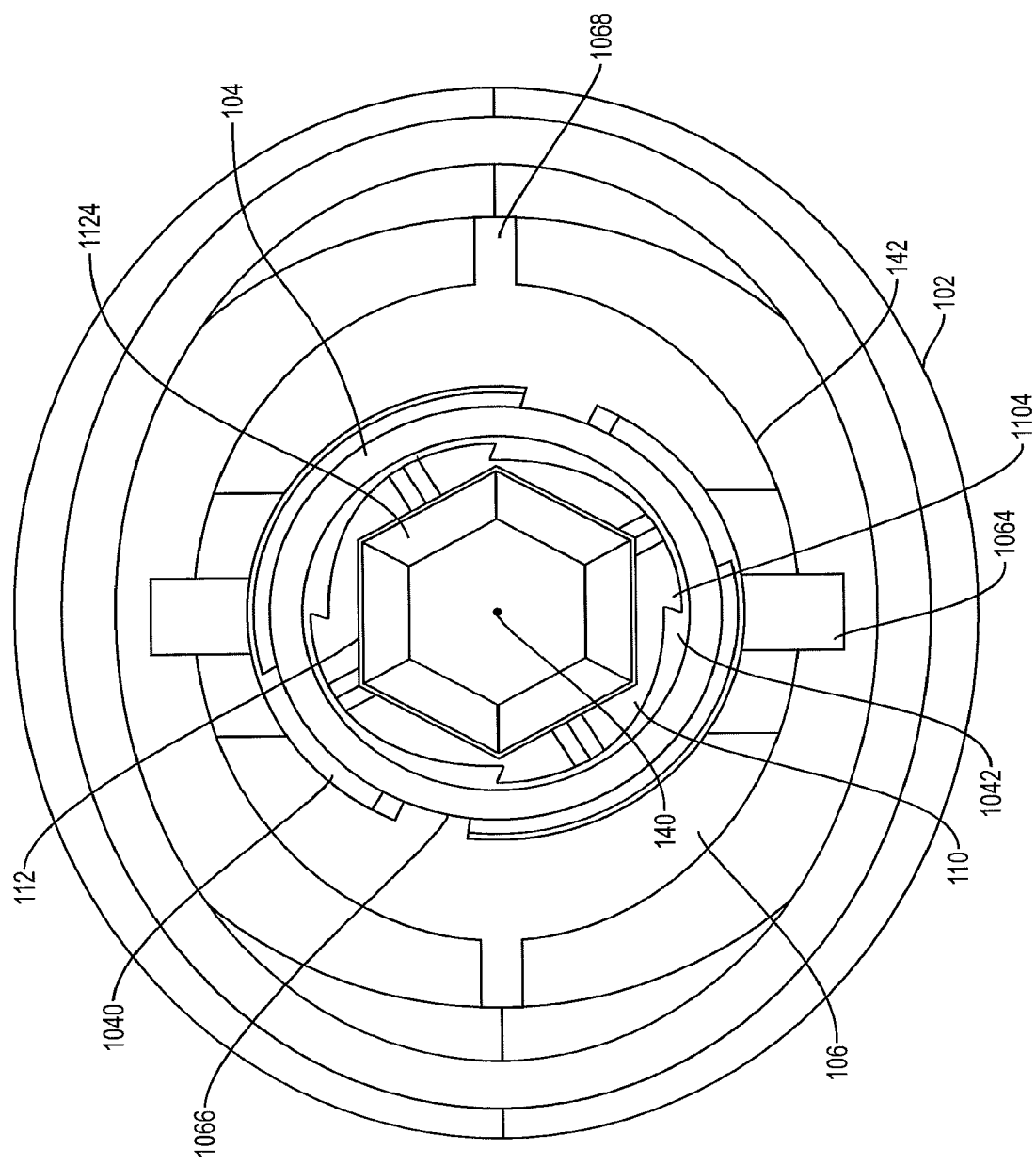
FIG. 5 is a cross-section top view of the injection device shown in FIG. 1A taken about line S-S shown in FIG. 1B.
Figure 6A:
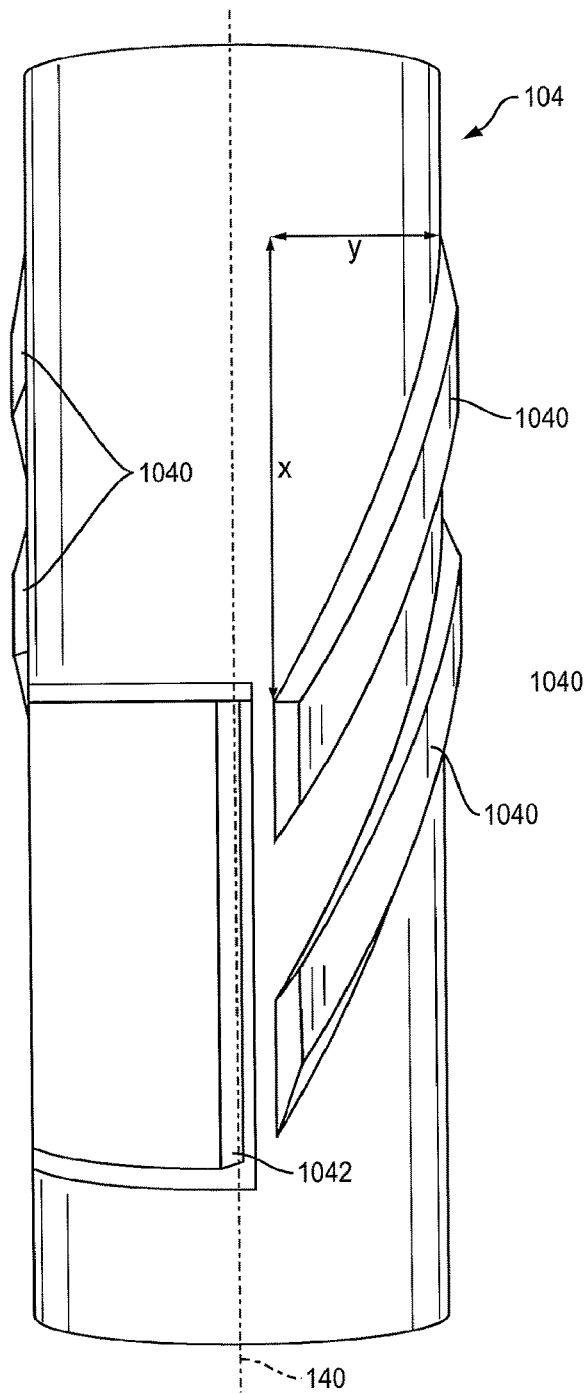
FIG. 6A is a side view of a twist driver of the injection device shown in FIG. 1A.
Figure 6B:
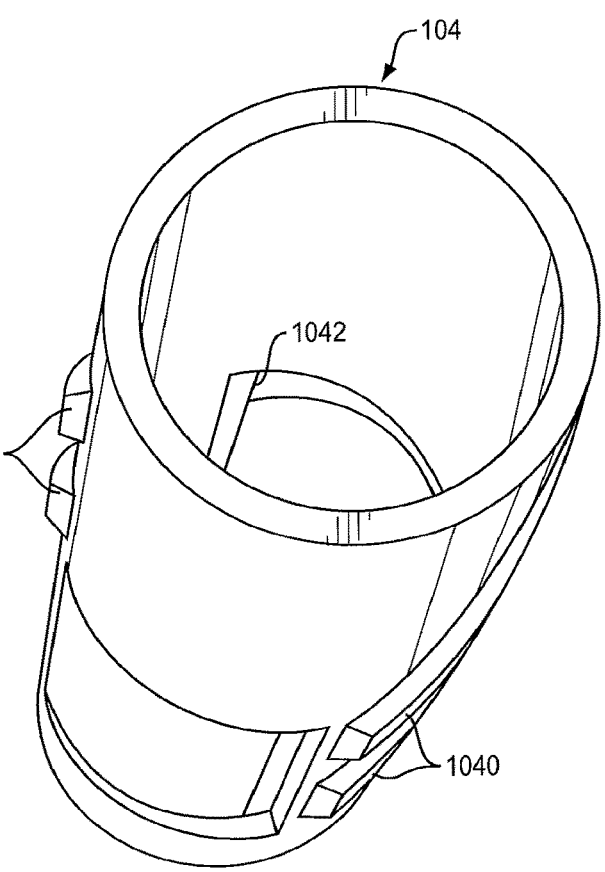
FIG. 6B is a perspective view of the twist driver shown in FIG. 6A.

Referring to FIG. 2B, in one embodiment, the dosage mechanism 132 also includes twist driver 104. With further reference to FIG. 5, in one embodiment, twist driver 104 is configured to be slideably engageable with trigger member 106 of push button 104. In one embodiment, twist driver 104 has threads 1040 disposed about its exterior surface. In one embodiment, threads 1040 of twist driver 104 engage threads 1066 of push button 142 such that firing motion of push button 142 along axis 140 relative to housing 102 causes twist driver 104 to axially rotate about axis 140 relative to housing 102 (which is counter-clockwise in the embodiment described herein). In one embodiment, twist driver 104 also includes ratchet flaps 1042. In certain embodiments, ratchet flaps 1042 of twist driver 104 engage driver 110 to cause movement of driver 110 in the desired firing direction (which is counter-clockwise in the embodiment described herein). FIGS. 6A and 6B disclose an exemplary embodiment of twist driver 104. In an alternative embodiment, twist driver 104 includes flexible protrusions rather than ratchet flaps 1042 that are configured to cause movement of driver 110 in a desired firing direction.

Referring to FIG. 2B, in one embodiment, the dosage mechanism 132 also includes driver 110. In one embodiment, a portion of driver 110 is configured to be fixed within twist driver 104 such that axial rotation of twist driver 104 about axis 140 relative to housing 102 causes rotation of driver 110 about axis 140 relative to housing 102. In one embodiment, a portion of both twist driver 104 and driver 110 are configured to fit within trigger member 106 of push button 142. In one embodiment, linear distal translation of push button 104 from a ready (or reset) state causes twist driver 104 to rotate about axis 140 relative to housing 102 (which is counter-clockwise in the embodiment described herein), which causes driver 110 to rotate about axis 140 relative to housing 102 in generally the same direction. With further reference to FIG. 5, in one embodiment, driver 110 includes lips 1104. In certain embodiments, lips 1104 are configured to engage ratchet flaps 1042 of twist driver 104 such the rotation of twist driver 104 about axis 140 relative to housing 102 causes ratchet flaps 1042 of twist driver 104 to engage lips 1104 of driver 110 to cause rotation of driver 110 in the same direction as twist driver 104.

Figure 7A:
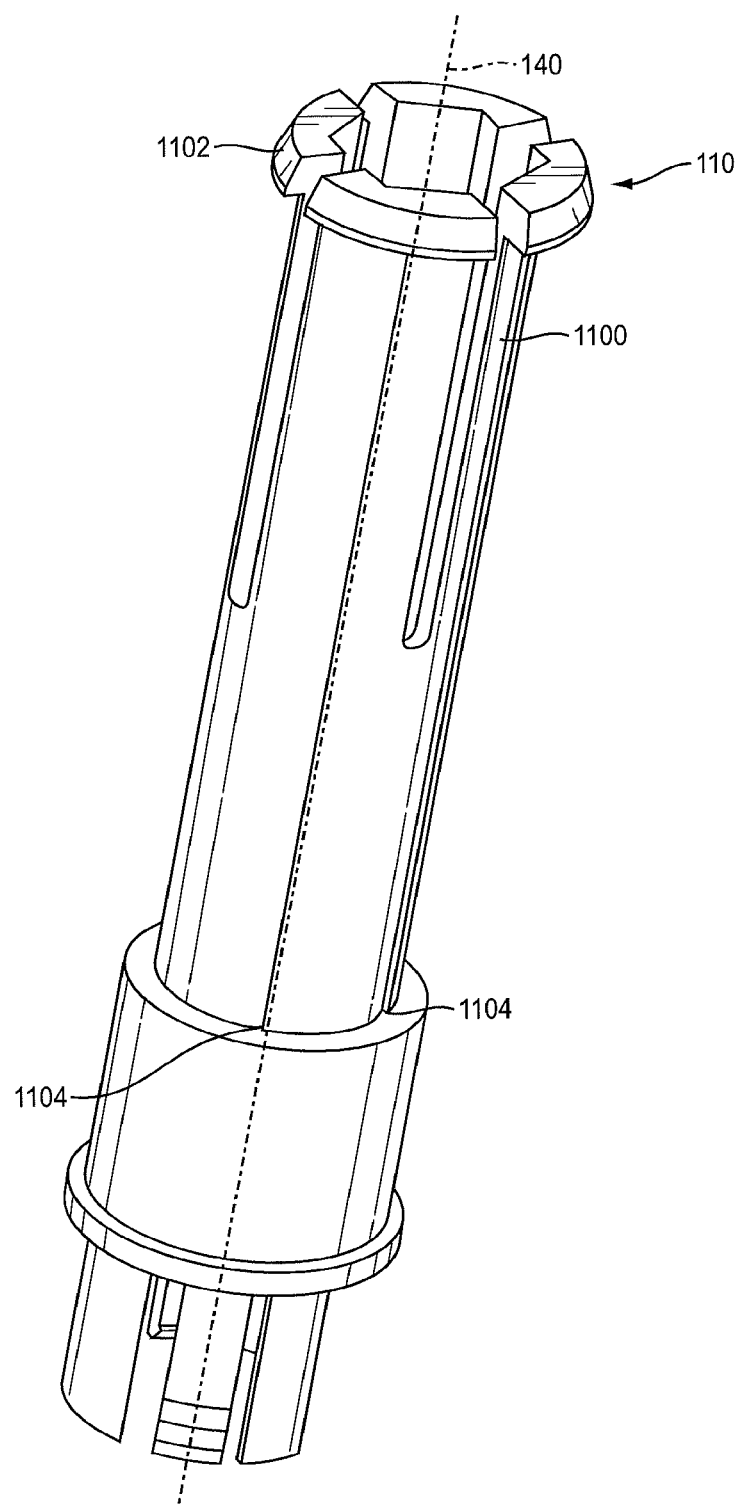
FIG. 7A is a perspective view of a driver of the injection device shown in FIG. 1A.
Figure 8:
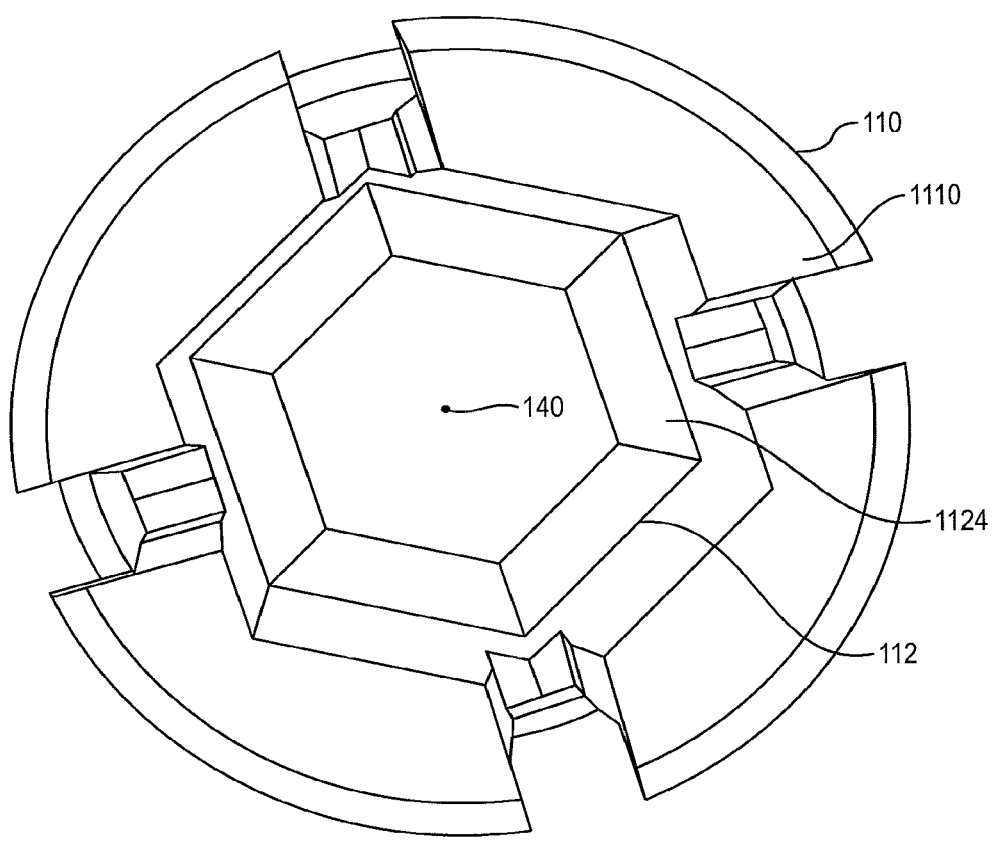
FIG. 8 is a top view of a driver and a plunger rod of the injection device shown in FIG. 1A.

Referring to FIGS. 7A-7C, in one embodiment, driver 110 includes legs 1100 at a proximal portion of driver 110. In one embodiment, each leg 1100 includes a flange 1102 at a proximal portion of leg 1100. As shown in FIG. 2B, force limiting biasing member 124 is situated on a top portion of flanges 1102 of driver 110. Further, as shown in FIG. 8, in one embodiment, the interior profile of driver 110 is polygonal shaped. In one embodiment, the interior profile of driver 110 is hexagonal shaped. In one embodiment, the interior profile of driver 110 is configured to engage plunger rod 112. In one embodiment, the interior profile of driver 110 is configured to engage a plunger head 1124 of plunger rod 112. In another embodiment, the interior profile of driver 110 is configured to allow plunger rod 112 to longitudinally translate along axis 140 relative to housing 102 and driver 110, restrict rotation about axis 140 relative to driver 110, and allow rotation about axis 140 relative to housing 102.

Referring to FIGS. 2A and 2B, in one embodiment, plunger rod 112 includes a plunger shaft 1126 and a plunger head 1124. In one embodiment, plunger shaft 1126 includes threads 1120 along the outside surface thereof that are configured to engage nut 114 (described in more detail below). In one embodiment, plunger shaft 1126 includes at least two threads 1120, each thread 1120, e.g., having a different thread pitch. In one embodiment, one of the at least two threads 1120 is configured to allow injection device 100 to self-prime. In one embodiment, plunger shaft 1126 has a circular cross-section. In other embodiments, plunger shaft 1126 has a non-circular cross-section. In one embodiment, plunger shaft 1126 has threaded segments 1120 separated by non-threaded segments 1122. In one embodiment, plunger rod 112 has a head 1124 at a proximal portion of plunger shaft 1126. In one embodiment, plunger head 1124 has polygonal cross-section. In another embodiment, plunger head 1124 has a hexagonal cross-section. In another embodiment, plunger head 1124 is sized and shaped to slideably engaged the interior surface of driver 110. In one embodiment, driver 110 is formed of at least two separate parts that can be affixed, for example by snap-fit, to each other. In one embodiment, plunger rod 112 is configured to rotate about axis 140 relative to housing 102 and distally translate along axis 140 relative to housing 102. In certain embodiments, plunger rod 112 has a washer 116 affixed to the distal end of plunger shaft 1126. With further reference to FIG. 1B, in one embodiment, washer 116 is configured to contact a proximal end of plunger 122. In another embodiment, washer 116 is configured to distribute loading on plunger 122 as plunger rod 112 distally translates along axis 140 relative to housing 102. In one embodiment, the distribution of load on plunger 122 causes plunger 122 to distally advance and expel a medicament dose from cartridge 120.

Figure 10:
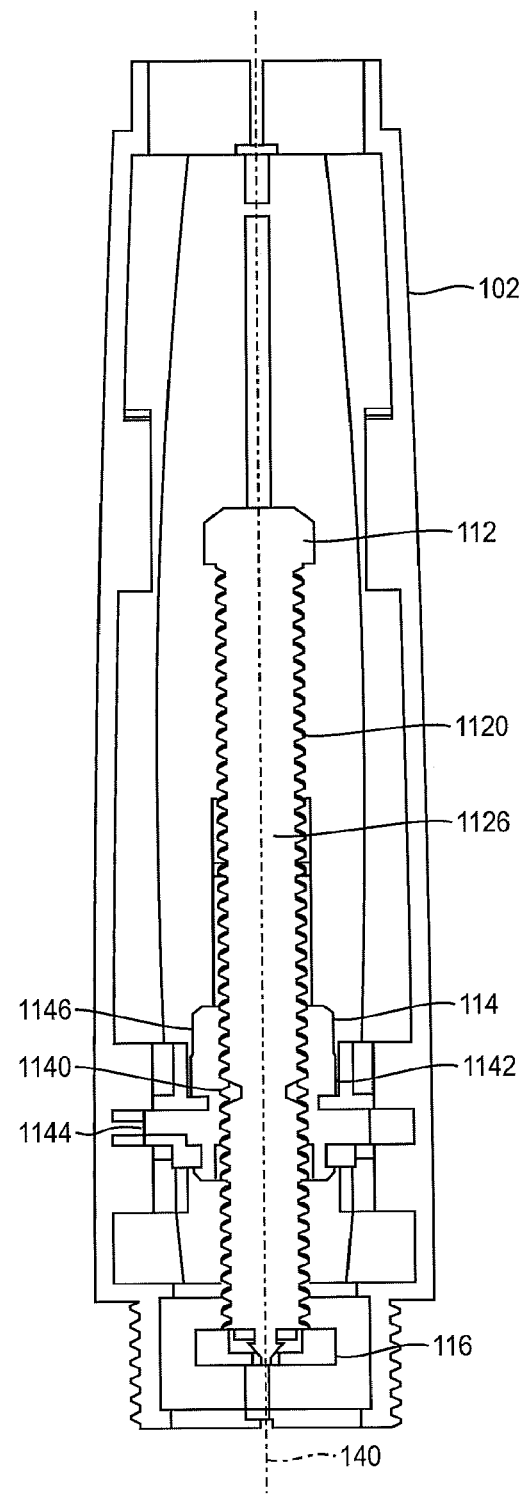
FIG. 10 is a cross-sectional side view of a housing, plunger rod and nut of the injection device shown in FIG. 1A.

Referring to FIG. 1B, in one embodiment, the dosage mechanism 132 includes nut 114. With further reference to FIGS. 9A and 9B, in one embodiment, nut 114 has a proximal portion 1146 and a distal portion 1144. In one embodiment, proximal portion 1146 is generally cylindrical shaped. In another embodiment, proximal portion 1146 has a plurality of ramps 1142 disposed about the outer surface of proximal portion 1146. As shown in FIG. 2A, ramps 1142 are configured to prevent driver 110 from rotating backwards due to friction with push button 142 while push button 142 is being moved through the resetting motion. In one embodiment, ramps 1142 are formed on proximal portion 1146. In one embodiment, ramps 1142 are arranged to allow movement of driver clip 108 in the desired firing direction (which is counter-clockwise in the embodiment described herein), but to engage legs 1080 of driver clip 108 (described in more detail below) after the firing step is completed to prevent driver clip 108 and driver 110 from being rotated in a direction opposite the firing direction. In another embodiment, proximal portion includes protrusions 1140 on an interior surface of proximal portion 1146. With further reference to FIG. 10, in one embodiment, protrusions 1140 are sized, shaped and configured to engage threads 1120 of plunger shaft 1126. In one embodiment, protrusions 1140 are sized, shaped and configured to engage threads 1120 of plunger shaft 1126 such that rotation of plunger rod 112 about axis 140 relative to housing 102 causes plunger rod 140 to longitudinally translate along axis 140 relative to housing 102. In one embodiment, distal portion 1144 of nut 114 is generally cylindrical shaped. In another embodiment, the diameter of distal portion 1144 of nut 114 is greater than the diameter of proximal portion 1146 of nut 114. As shown in FIG. 1B, in one embodiment, nut 114 is fixed to housing 102. In one embodiment, distal portion 1144 of nut 114 is fixed to housing 102. In one embodiment, distal portion 1144 of nut 114 is fixed to housing 102 within slots that are integrally formed with housing 102. In another embodiment, distal portion 1144 of nut 114 is fixed via mating pins and recesses provided on distal portion 1144 and housing 102 and fixedly secured together during manufacture, such as via adhesives or ultrasonic welding.

Referring to FIGS. 2A and 2B, in one embodiment, the dosage mechanism 132 further includes driver clip 108. In one embodiment, driver clip 108 connects driver 110 and nut 114. In one embodiment, driver clip 108 connects to driver 110 with the use of clips and apertures contained on both driver clip 108 and driver 110. In one embodiment, driver clip 108 includes legs 1080. In one embodiment, legs 1080 are configured to connect to proximal portion 1146 of nut 114. In one embodiment, driver clip legs 1080 having bottom surfaces that engage a top surface of distal portion 1144 of nut 104. In one embodiment, driver clip 108 moves in concert with driver 110. In other words, in one embodiment, driver clip 108 rotates about axis 140 relative to housing 102 when driver 110 rotates about axis 140 relative to housing 102.

Referring to FIG. 5, in one embodiment, during firing motion of push button 142, i.e., movement of push button 142 distally along axis 140 from a ready (or reset) state towards a fired state, threads 1066 of push button 142 engage threads 1040 of twist driver 104, causing twist driver 104 to rotate about axis 140 relative to housing 102 in a first direction (which is counter-clockwise in the embodiment described herein). In an alternative embodiment, push button 142 has one or more projections, rather than threads 1066, which engage the threads of 1040 of twist driver during firing motion of push button 142, causing twist driver 104 to rotate about axis 140 relative to housing 102 in a first direction. In one embodiment, during rotation of twist driver 104, flaps 1042 of twist driver 104 engage lips 1104 of driver 110, causing driver 110 to rotate in generally the same direction as twist driver 104. In one embodiment, plunger rod 112 is disposed within driver 110 such that plunger head 1124 is engaged with the interior surface of driver 110 and rotation of driver 110 causes plunger rod 112 to rotate in general the same direction as driver 110. With further reference to FIG. 10, in one embodiment, threads 1120 of plunger rod 112 are threadably engaged with protrusions 1140 of nut 114, such that rotation of plunger rod 112 about axis 140 relative to housing 102 causes plunger rod 112 to distal advance along axis 140 relative to housing 102. As shown in FIG. 1B, in one embodiment, the distal advancement of plunger rod 112 along axis 140 relative to housing 102 causes washer 116, which is disposed at a distal end of plunger rod 116, to distally displace plunger 112 of cartridge 120 and expel medicament from cartridge 120.

Referring to FIG. 5, in one embodiment, during resetting motion of push button 142, i.e., movement of push button 142 distally along axis 140 from a fired state to a ready (or reset) state, the engagement of threads 1066 of push button 142 and threads 1040 of twist driver 104 causes twist driver 104 to rotate about axis 140 relative to housing 102 in a second direction which is opposite the first direction, e.g., cause rotation of twist driver 104 in a clockwise manner. In one embodiment, rotation of twist driver 104 in the second direction causes flaps 1042 of twist driver 104 to disengage lips 1104 of driver 110 such that the rotation of twist driver 104 does not cause any movement of driver 110 and allows for push button 142 to reset with movement of plunger rod 112. However, in certain embodiments, even with the disengagement of the flaps 1042 of twist driver 104 and lips 1104 of driver 1104, friction between twist driver 104 and driver 110 causes driver 110 to move in the same direction as twist driver 104 during resetting motion. With additional reference to FIGS. 2A and 2B, in certain embodiments, driver clip 108, which is connected to driver 110 such that driver 110 and driver clip move as a unitary piece, engages ramps 1142 of nut 114 during movement of driver 110 in the second direction to prevent driver 110 from rotating backwards.

In one embodiment, during the firing and resetting motions of push button 142, the distance moved by push button 142 is greater than the rotational distance of twist driver 104.

Figure 11:
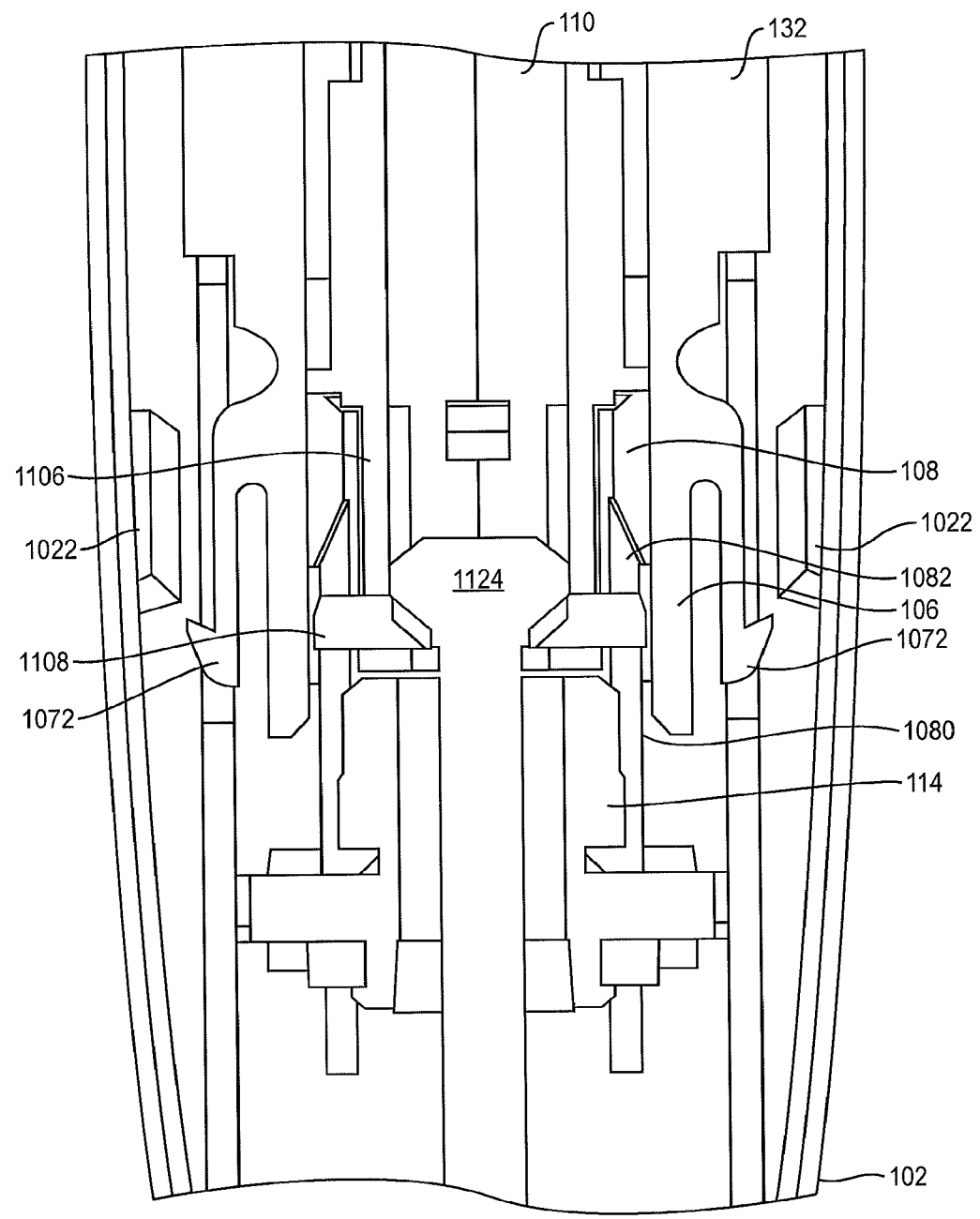
FIG. 11 is a cross-sectional side view of a lock-out feature of the injection device shown in FIG. 1A.

Referring to FIG. 11, in one embodiment, injection device 100 includes a final lockout mechanism. In one embodiment, the lockout mechanism disables injection device 100 from further motion of dosing mechanism 132 once the final dose has been administered. In one embodiment, once the final dose has been administered, head 1124 of plunger rod 112 moves to a position such that it is adjacent the proximal surface of nut 114. In one embodiment, driver 110 includes at least one arm 1106 that is resiliently flexible and structured to extend outwardly when head 1124 of plunger rod 112 is adjacent the proximal surface of nut. In one embodiment, when head 1124 forces arm 1106 outwardly, foot 1108, which is affixed to the distal end of arm 1106, extends outwardly into notch 1082 formed between legs 1080 of drive clip 108. In one embodiment, the extended foot 1108 extends outwardly a bottom portion of trigger member 106, which is resiliently flexible. In one embodiment, the bottom portion of trigger member 106 includes a hook 1072. In one embodiment, the extension of the bottom portion of trigger member 106 extends hook 1072 to align with protrusions 1022 of housing 102 such that any proximal movement of push button 142 will cause hook 1072 to engage protrusions 1022, which are integrally formed in housing 102. In one embodiment, this prevents any movement of push button 142 and disables injection device 100, preventing accidental or intentional further use.

While dosing mechanism 132 described herein is shown as a part of a needled injection device for a liquid medicament, it is understood that the mechanism can be used in other dispensing devices that include a dispenser that is actuated by linear motion. This includes injection devices that use a mechanism other than a push button as well as other dispensing devices for gels or the like which may or may not contain a medicament.

In one embodiment, the dose size is varied by the geometry of the threads 1120 of plunger rod 112. That is, in one embodiment, by increasing the pitch of thread 1120, the linear distance traveled by plunger rod 112 upon a single dose rotation, and therefore plunger 122, is increased, leading to a greater dose size. Conversely, in one embodiment, by decreasing the pitch of thread 1120, the dose size is reduced. In one embodiment, the dose size is varied by changing the diameter of cartridge 120. In one embodiment, a larger diameter of cartridge 120 will increase the dose size. In another embodiment, a smaller diameter of cartridge 120 will decrease the dose size. In one embodiment, these factors can be adjusted to derive an injector that contains a desired amount of liquid medicament and will produce the desired number of doses at a desired, fixed, amount, and will have the desired dosing and resetting motions.

Each and every reference identified herein is incorporated by reference in its entirety. The entire disclosure of U.S. patent application publication number 2010/0036320 is hereby incorporated herein by reference thereto as if fully set forth herein. The term "about," as used herein, should generally be understood to refer to both the corresponding number and a range of numbers. Moreover, all numerical ranges herein should be understood to include each whole integer within the range.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

The invention claimed is:

1. An injector comprising:
a housing having a proximal-distal axis, the housing configured to receive a medicament cartridge;
a plunger rod having a screw thread and configured to advance along the proximal-distal axis relative to the housing to dispense medicament from the medicament cartridge;
an activation mechanism moveable along the proximal-distal axis relative to the housing;
a twist driver threadably engaged with the activation mechanism such that movement of the activation mechanism towards a distal end of the housing causes rotation of the twist driver about the proximal-distal axis;
a flexible column coupled to the activation mechanism, the flexible column configured to engage the housing to limit movement of the activation mechanism to one direction along the proximal-distal axis; and
a driver engaged with the twist driver such that rotation of the twist driver causes rotation of the driver, the driver also engaged with a portion of the plunger rod such that rotation of the driver causes rotation of the plunger rod, advancing the plunger rod along the proximal-distal axis relative to the housing.

2. The injector of claim 1, wherein the medicament includes a parathyroid hormone.

3. The injector of claim 2, wherein the parathyroid hormone is triparatide.

4. The injector of claim 1, further comprising:
an anti-reverse mechanism including:
at least one ratchet integrally formed on an internal surface of the housing; and
the flexible column, wherein the flexible column includes a flexible column protrusion at a proximal end thereof,
wherein as the activation mechanism moves along the proximal-distal axis, the flexible column protrusion engages the at least one ratchet and restricts movement of the activation mechanism to one direction during a firing motion and a resetting motion.

5. The injector of claim 4, wherein the flexible column protrusion is generally elliptically shaped.

6. The injector of claim 4, wherein the activation mechanism includes a protrusion configured to engage the housing such that the activation mechanism is prevented from moving along the proximal-distal axis after an injection.

7. The injector of claim 1, wherein the activation mechanism includes a sidewall with an opening in the sidewall.

8. The injector of claim 7, wherein at least a portion of the flexible column is positioned within the opening.

9. The injector of claim 1, further comprising:
a nut fixated within the housing having protrusions on an internal surface that engage the screw thread of the plunger rod such that as the plunger rod rotates, the plunger rod is advanced along the proximal-distal axis relative to the housing.

10. The injector of claim 1, wherein the twist driver further includes a ratchet flap that is configured to engage a lip of the driver such that the twist driver can axially rotate about the proximal-distal axis in generally only one direction.

11. The injector of claim 1, further comprising a biasing member disposed within the activation mechanism to facilitate movement of the activation mechanism from a fired position to a reset position.

12. The injector of claim 1, wherein the housing includes a cartridge sleeve releasably coupled to housing, the cartridge sleeve configured to hold the medicament cartridge.

13. The injector of claim 12, further comprising
a needle assembly releasably coupled to the cartridge sleeve, the needle assembly in fluid communication with the medicament cartridge.

14. The injector of claim 1, wherein the plunger rod includes a first thread having a first thread pitch and a second thread having a second thread pitch, the first thread pitch being different from the second thread pitch.

15. The injector of claim 14, wherein the first thread pitch is configured such that the injector self-primes upon initial movement of the activation mechanism.

16. The injector of claim 1, wherein the activation mechanism comprises a user-operable push button.

17. The injector of claim 1, wherein the activation mechanism includes a protrusion configured to engage the housing such that the activation mechanism is prevented from moving along the proximal-distal axis.

* * * * *